(12) United States Patent
Byun et al.

(10) Patent No.: US 10,787,690 B2
(45) Date of Patent: Sep. 29, 2020

(54) **MICROORGANISM OF THE GENUS *CORYNEBACTERIUM* PRODUCING L-LYSINE AND A METHOD FOR PRODUCING L-LYSINE USING THE SAME**

(71) Applicant: CJ CHEILJEDANG CORPORATION, Seoul (KR)

(72) Inventors: Hyo Jeong Byun, Suwon-si (KR); Hyung Joon Kim, Seoul (KR); Hyun Won Bae, Suwon-si (KR); Song-Gi Ryu, Suwon-si (KR); Hyang Choi, Suwon-si (KR); Jun Ok Moon, Yongin-si (KR); Kyung-Chang Lee, Suwon-si (KR); Yunjung Choi, Suwon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/461,327

(22) PCT Filed: Sep. 19, 2017

(86) PCT No.: PCT/KR2017/010243
§ 371 (c)(1),
(2) Date: May 15, 2019

(87) PCT Pub. No.: WO2018/093033
PCT Pub. Date: May 24, 2018

(65) Prior Publication Data
US 2019/0352683 A1    Nov. 21, 2019

(30) Foreign Application Priority Data
Nov. 15, 2016   (KR) .................. 10-2016-0152037

(51) Int. Cl.
*C12P 13/08* (2006.01)
*C12R 1/16* (2006.01)

(52) U.S. Cl.
CPC ............... *C12P 13/08* (2013.01); *C12R 1/16* (2013.01)

(58) Field of Classification Search
None
See application file for complete search history.

(56) References Cited

U.S. PATENT DOCUMENTS

2005/0244935 A1   11/2005   Pompejus et al.
2016/0016902 A1   1/2016    Chen

FOREIGN PATENT DOCUMENTS

| JP | 2002-191370 A | 7/2002 |
|---|---|---|
| KR | 10-0073610 B1 | 2/1994 |
| KR | 10-0397322 B1 | 9/2003 |
| KR | 10-0838038 B1 | 6/2008 |
| KR | 10-0924065 B1 | 10/2009 |
| KR | 10-0930203 B1 | 12/2009 |
| KR | 10-1498630 B1 | 3/2015 |

OTHER PUBLICATIONS

NCBI Accession No. NP_599648.1, glycosyltransferase [Corynebacterium glutamicum ATCC 13032] (2 pages) (Aug. 3, 2016).
Vetting et al., "Structural and Enzymatic Analysis of MshA from *Corynebacterium glutamicum*," *Journal of Biological Chemistry* 283(23):15834-15844 (Jun. 6, 2008).

*Primary Examiner* — Suzanne M Noakes
(74) *Attorney, Agent, or Firm* — Seed IP Law Group LLP

(57) ABSTRACT

The present disclosure relates to a microorganism producing L-lysine, and a method for producing L-lysine using the same.

4 Claims, No Drawings
Specification includes a Sequence Listing.

SEQUENCE LISTING

```
<160> NUMBER OF SEQ ID NOS: 16

<210> SEQ ID NO 1
<211> LENGTH: 418
<212> TYPE: PRT
<213> ORGANISM: Artificial Sequence
<220> FEATURE:
<223> OTHER INFORMATION: HM1524 amino acid

<400> SEQUENCE: 1

Met Arg Val Ala Met Ile Ser Met His Thr Ser Pro Leu Gln Gln Pro
1               5                   10                  15

Gly Thr Gly Asp Ser Gly Gly Met Asn Val Tyr Ile Leu Ser Thr Ala
                20                  25                  30

Thr Glu Leu Ala Lys Gln Gly Ile Glu Val Asp Ile Tyr Thr Arg Ala
            35                  40                  45

Thr Arg Pro Ser Gln Gly Glu Ile Val Arg Val Ala Glu Asn Leu Arg
        50                  55                  60

Val Ile Asn Ile Ala Ala Gly Pro Tyr Glu Gly Leu Ser Lys Glu Glu
```

```
                65                  70                  75                  80
Leu Pro Thr Gln Leu Ala Ala Phe Thr Gly Gly Met Leu Ser Phe Thr
                    85                  90                  95

Arg Arg Glu Lys Val Thr Tyr Asp Leu Ile His Ser His Tyr Trp Leu
                100                 105                 110

Ser Gly Gln Val Gly Trp Leu Leu Arg Asp Leu Trp Arg Ile Pro Leu
                115                 120                 125

Ile His Thr Ala His Thr Leu Ala Ala Val Lys Asn Ser Tyr Arg Asp
            130                 135                 140

Asp Ser Asp Thr Pro Glu Ser Glu Ala Arg Arg Ile Cys Glu Gln Gln
145                 150                 155                 160

Leu Val Asp Asn Ala Asp Val Leu Ala Val Asn Thr Gln Glu Glu Met
                165                 170                 175

Gln Asp Leu Met His His Tyr Asp Ala Asp Pro Asp Arg Ile Ser Val
                180                 185                 190

Val Ser Pro Gly Ala Asp Val Glu Leu Tyr Ser Pro Gly Asn Asp Arg
                195                 200                 205

Ala Thr Glu Arg Ser Arg Arg Glu Leu Gly Ile Pro Leu His Thr Lys
            210                 215                 220

Val Val Ala Phe Val Gly Arg Leu Gln Pro Phe Lys Gly Pro Gln Val
225                 230                 235                 240

Leu Ile Lys Ala Val Ala Ala Leu Phe Asp Arg Asp Pro Asp Arg Asn
                245                 250                 255

Leu Arg Val Ile Ile Cys Gly Gly Pro Ser Gly Pro Asn Ala Thr Pro
                260                 265                 270

Asp Thr Tyr Arg His Met Ala Glu Glu Leu Gly Val Glu Lys Arg Ile
            275                 280                 285

Arg Phe Leu Asp Pro Arg Pro Ser Glu Leu Val Ala Val Tyr Arg
290                 295                 300

Ala Ala Asp Ile Val Ala Val Pro Ser Phe Asn Glu Ser Phe Gly Leu
305                 310                 315                 320

Val Ala Met Glu Ala Gln Ala Ser Gly Thr Pro Val Ile Ala Ala Arg
                325                 330                 335

Val Gly Gly Leu Pro Ile Ala Val Ala Glu Gly Glu Thr Gly Leu Leu
                340                 345                 350

Val Asp Gly His Ser Pro His Ala Trp Ala Asp Ala Leu Ala Thr Leu
                355                 360                 365

Leu Asp Asp Asp Glu Thr Arg Ile Arg Met Gly Glu Asp Ala Val Glu
            370                 375                 380

His Ala Arg Thr Phe Ser Trp Ala Ala Thr Ala Ala Gln Leu Ser Ser
385                 390                 395                 400

Leu Tyr Asn Asp Ala Ile Ala Asn Glu Asn Val Asp Gly Glu Thr His
                405                 410                 415

His Gly

<210> SEQ ID NO 2
<211> LENGTH: 1257
<212> TYPE: DNA
<213> ORGANISM: Artificial Sequence
<220> FEATURE:
<223> OTHER INFORMATION: HM1524 nucleotide

<400> SEQUENCE: 2
atgcgcgtag ctatgatttc catgcacacc tctccattgc agcagcccgg aactggtgat    60
```

-continued

```
tcaggcggca tgaacgtcta cattctttcg accgcgactg agctagcgaa acagggtatc    120
gaggtcgata tttacactcg tgccacgagg ccttctcagg gtgagatcgt gagagtagct    180
gagaatttgc gggtcattaa tatcgctgcg gggccgtatg aggggctttc caaagaggag    240
cttcctactc agttggcggc gtttaccggc ggaatgttgt cgtttacgcg ccgggagaag    300
gttacttatg atctgatcca ttctcactat tggctgtctg gtcaggtggg gtggttgctg    360
cgcgatttgt ggcggattcc ccttattcat acggcacaca ctttggcggc ggtgaagaat    420
tcttatcggg atgattcgga cactccggag tcggaggcgc gtcgcatttg tgagcagcag    480
ctggtggata cgctgacgt gttggcggtg aacactcagg aggagatgca ggatttgatg    540
catcactacg atgcggatcc ggatcggatt tctgtggtgt caccgggtgc ggacgtggaa    600
ctttatagcc ctggaaatga tcgcgcgacg gaacgttccc gtcgtgagct gggcattccg    660
ctgcacacaa aggtagtggc ttttgtgggt cggttgcagc cgtttaaggg cccgcaggtg    720
ctgatcaagg cggttgcggc gttgtttgat cgcgatccgg accgaaatct gcgcgtcatt    780
atttgtggcg gcccttctgg tccgaatgcg acaccggata cctataggca tatgcagag    840 gaactgggcg tcgaaaagcg aattcgcttt ttggacccgc gcccgccgag cgagctagtg    900
gccgtgtatc gggcggcgga catcgtggcc gtgccaagtt ttaatgagtc cttcggactc    960
gtcgccatgg aggcgcaagc cagcggcaca ccggtcattg cggcccgggt tggcggcctg   1020
cccatcgcag tcgcggaagg ggagacggga ttgcttgtcg acggccactc cccgcatgcc   1080
tgggccgacg ccttagccac actcttggac gatgacgaaa cgcgcatcag aatgggtgaa   1140
gacgccgtcg aacacgccag aacattctcc tgggcggcca ccgccgcaca gctatcgtcg   1200
ctgtacaacg acgctattgc caacgaaaat gtcgacggtg aaacgcatca cggctaa      1257
```

```
<210> SEQ ID NO 3
<211> LENGTH: 19
<212> TYPE: DNA
<213> ORGANISM: Artificial Sequence
<220> FEATURE:
<223> OTHER INFORMATION: WT genomic DNA library primer-1

<400> SEQUENCE: 3
acgacgggat cagtaccga                                                   19

<210> SEQ ID NO 4
<211> LENGTH: 19
<212> TYPE: DNA
<213> ORGANISM: Artificial Sequence
<220> FEATURE:
<223> OTHER INFORMATION: WT genomic DNA library primer-2

<400> SEQUENCE: 4
agctatctgt cgcagcgcc                                                   19

<210> SEQ ID NO 5
<211> LENGTH: 28
<212> TYPE: DNA
<213> ORGANISM: Artificial Sequence
<220> FEATURE:
<223> OTHER INFORMATION: 5' XhoI primer

<400> SEQUENCE: 5
tcactcgagt gatggccagg ttgttgtc                                         28

<210> SEQ ID NO 6
<211> LENGTH: 29
```

```
<212> TYPE: DNA
<213> ORGANISM: Artificial Sequence
<220> FEATURE:
<223> OTHER INFORMATION: 3' XhoI primer

<400> SEQUENCE: 6
tcactcgagt tagtcatagg tactagttt                              29

<210> SEQ ID NO 7
<211> LENGTH: 29
<212> TYPE: DNA
<213> ORGANISM: Artificial Sequence
<220> FEATURE:
<223> OTHER INFORMATION: 5' EcoRI primer

<400> SEQUENCE: 7
tcagaattct tccttcaggc taatctttt                              29

<210> SEQ ID NO 8
<211> LENGTH: 29
<212> TYPE: DNA
<213> ORGANISM: Artificial Sequence
<220> FEATURE:
<223> OTHER INFORMATION: 3' NdeI primer

<400> SEQUENCE: 8
tcacatatgt gtttcctttc gttgggtac                              29

<210> SEQ ID NO 9
<211> LENGTH: 29
<212> TYPE: DNA
<213> ORGANISM: Artificial Sequence
<220> FEATURE:
<223> OTHER INFORMATION: 5' SpeI primer

<400> SEQUENCE: 9
tcaactagtc ttccttcagg ctaatcttt                              29

<210> SEQ ID NO 10
<211> LENGTH: 29
<212> TYPE: DNA
<213> ORGANISM: Artificial Sequence
<220> FEATURE:
<223> OTHER INFORMATION: 3' SalI primer

<400> SEQUENCE: 10
tcagtcgact gtttcctttc gttgggtac                              29

<210> SEQ ID NO 11
<211> LENGTH: 26
<212> TYPE: DNA
<213> ORGANISM: Artificial Sequence
<220> FEATURE:
<223> OTHER INFORMATION: s-NdeI primer

<400> SEQUENCE: 11
tcacatatgc gcgtagctat gatttc                                 26

<210> SEQ ID NO 12
<211> LENGTH: 29
<212> TYPE: DNA
<213> ORGANISM: Artificial Sequence
<220> FEATURE:
<223> OTHER INFORMATION: t-SpeI primer

<400> SEQUENCE: 12
```

```
tcaactagtt tagccgtgat gcgtttcac                                         29
```

<210> SEQ ID NO 13
<211> LENGTH: 20
<212> TYPE: DNA
<213> ORGANISM: Artificial Sequence
<220> FEATURE:
<223> OTHER INFORMATION: HM1524 selection primer-1

<400> SEQUENCE: 13

```
gtcgaacacg ccagaacatt                                                   20
```

<210> SEQ ID NO 14
<211> LENGTH: 20
<212> TYPE: DNA
<213> ORGANISM: Artificial Sequence
<220> FEATURE:
<223> OTHER INFORMATION: HM1524 selection primer-2

<400> SEQUENCE: 14

```
tactctcacg atctcaccct                                                   20
```

<210> SEQ ID NO 15
<211> LENGTH: 4102
<212> TYPE: DNA
<213> ORGANISM: Artificial Sequence
<220> FEATURE:
<223> OTHER INFORMATION: pEC-H15

<400> SEQUENCE: 15

```
gatcggatac ggctcagtcc actacgtttc ccacaccgga agggaaggcg attggtttca       60
gtgtggtttc agcccggcga agtccaaaat ctgcctgtat ggcctgaagg attcgcctcg      120
cggtgaggaa ttgctgcaga aacttggaaa atacaccgaa ggccgcggat gcgtgtacat      180
caataaaccg gaagacatcg atttggatgt tttagaggcc atgatcagcg agtcatgggc      240
cggccaaggc taggttgcaa atccccacca caagttgctc tgatcagcga ttttgtggtg      300
gattttttgcg tctccgccac ctgaaaccgc aaggattcac cacagattcg agttttcctt      360
tgaaacgtgg tggatccttg ccctgcaaac tttcaggaat cacaccagtc ccactggcca      420
caaatgggaa acccctcaga atcgcttctg aggggttatc tagcgccagt tggggtaagt      480
gcccatttgg gaaactcgac ctcttaaatc ggcgtctact tgccgagctt cttcaacgtc      540
cactcgtgcg gggcctgagt tgcaaatccc caccacaaat tgctctgatt agtggatttg      600
tggtggatttt ttgcgtcttc gctatctgaa accgcgagga tccaccacag attcgagttt      660
tcctttgaaa cgtggttgat ccttgccctg gaatctttca ggaatcacat cagtcccact      720
ggttacaaag tggaaacccc tcagaatcgc ttctgggggg tgaactagcg ccagttgggg      780
taagtgccca tttgggaaac tcgacctctt aaatcggcgt ctacttgccg agcttcttca      840
acaactccgc ctgcacttca cgacgcctaa tcttgcccat ctgatcccgc ggcatctcct      900
caaagtggta gaaagtgcgc ggaaccttgt agcgggtgag gttcttgcgg gcgaattcct      960
tcaggccatc cggatccagc gctgcacctt ccaccaaagt gatggcagca acgacgtttt     1020
cggagccgtc ttcacgcggg ataccaacga ctgcggaatc ttcaatgtct gggtgctctg     1080
cgaggacttc ttcaacctca gctgggtaca cgttgaaacc gccagtgatg atgacttcct     1140
tgatgcgagc aactaggcgg atgaaccccgt cttcttccat cactccgacg tcgccggtgc     1200
ggtaccactc gccgtggaag ctgttcttgg tggcttcttc ctggttgagg taacccttga     1260
acacctgtgg gcccttgact aggacttcgc cttcgctgcc gtcgggcatg gtttcgtcga     1320
```

```
ggttttctgg gtttgcgatg cgcacgatgg tgtcggggaa ggggattcct acgtagcctt    1380
ggcgtcggtg atcgctcatg gggttaccca cgatgatggg ggaggtttcg gtgaggccgt    1440
agccttcgac gaggcgtccg ccggtgtgct tttcccagcg ttcaacggtg cgctgggaga    1500
gtgtggatgc accggagaag gcgttgcgga ctcccttgat ggggattcct tcttttcgg    1560 aggcgtcgac gattttttcg taaagggtgg gcacgcctgg tagccaggtt ggggtgtgct    1620
ttttcattac gttcatgatc aggtcgatgc gtggggtggg aagtagcacc atttcgccac    1680
cgatgaacac ggacagtgtg ccgaccatgg tcagaccgta tgcgtggaac attggtaggg    1740
ctgcaagcat gcgttctggt ttgtctccga gacctggaac ccagtgcttt ccttggagga    1800
gattggagaa caggtttccg tgggtgagct gggcacccct ggggcgtccg gtggtgccgg    1860
aggtgtagag gatcagcgcg acggattctt tggtcacggt gggttctgaa actacgtcgt    1920
cgccgtcgcc gcccattgct gcgctggtca gggtttcaaa aggaacggtg ttggggctg    1980 cgccggagag ggattcgcgg ctcttgcgca gtgcagggat tgggagccga agtgctaggc    2040
gctggagtgg tggcatcgcg ttgatcatgt tgaccgacac gatggtttcc aactgggtct    2100
gtccacgtag ctgttcgacg gtggggggagg ctttgtccca gacgatggca acgcgggcac    2160
cgtggtcttt gaagggttcg agcagttcgt gggcggtgta gagcgggttg tgctcaatga    2220
ctactgcgcc gagtttcagc actgcgtaga aagctgcgat gtgctgtggg cagttgggga    2280
ggataatcgc tacgtgatcg ccggggcgga cacctagtgc gcgcaggcca gcggcagttt    2340
tgcggacttc tttgtccagt tcaccgtagg tttgtgaacg accgaaaaag taggtggctg    2400
gcttgtctgc gttgatggcc aggttgttgt cgtaaacgtc cagcagggtg gtgtcgccat    2460
attccagcga gtgtggcgtc cactctgggt agtgctggag ccattctttg gtttcgtatg    2520
ctgacatggt gtcccttcaa ctgcgttgct ttagtgccct ttagtatata gagacgtccc    2580
gctgctttct tcggcgatct agaatgtggg catgcgcgta gctatgattt ccatgcacac    2640
ctctccattg cagcagcccg gaactggtga ttcaggcggc atgaacgtct acattctttc    2700
gaccgcgact gagctagcga aacagggtat cgaggtcgat atttacactc gtgccacgag    2760
gccttctcag ggtgagatcg tgagagtagc tgagaatttg cgggtcatta atatcgctgc    2820
ggggccgtat gagggctttt ccaaagagga gcttcctact cagttggcgg cgtttaccgg    2880
cggaatgttg tcgtttacgc gccgggagaa ggttacttat gatctgatcc attctcacta    2940
ttggctgtct ggtcaggtgg ggtggttgct gcgcgatttg tggcggattc cccttattca    3000
tacggcacac actttggcgg cggtgaagaa ttccttatcgg gatgattcgg acactccgga    3060
gtcggaggcg cgtcgcattt gtgagcagca gctggtggat aacgctgacg tgttggcggt    3120
gaacactcag gaggagatgc aggatttgat gcatcactac gatgcggatc cggatcggat    3180
ttctgtggtg tcaccgggtg cggacgtgga actttatagc cctggaaatg atcgcgcgac    3240
ggaacgttcc cgtcgtgagc tgggcattcc gctgcacaca aaggtagtgg cttttgtggg    3300
tcggttgcag ccgtttaagg gcccgcaggt gctgatcaag gcggttgcgg cgttgtttga    3360
tcgcgatccg gaccgaaatc tgcgcgtcat tatttgtggc ggcccttctg gtccgaatgc    3420
gacaccggat acctataggc atatggcaga ggaactgggc gtcgaaaagc gaattcgctt    3480
tttggacccg cgcccgccga gcgagctagt ggccgtgtat cgggcggcgg acatcgtggc    3540
cgtgccaagt tttaatgagt ccttcggact cgtcgccatg gaggcgcaag ccagcggcac    3600
accggtcatt gcggcccggg ttggcggcct gcccatcgca gtcgcggaag gggagacggg    3660
```

```
attgcttgtc gacggccact ccccgcatgc ctgggccgac gccttagcca cactcttgga    3720
cgatgacgaa acgcgcatca gaatgggtga agacgccgtc gaacacgcca gaacattctc    3780
ctgggcggcc accgccgcac agctatcgtc gctgtacaac gacgctattg ccaacgaaaa    3840
tgtcgacggt gaaacgcatc acggctaagt aaacgcgcgt cgtggaacat aaagtggcaa    3900
actagtacct atgactaacg gaaaattgat tcttcttcgt cacggtcaga gcgaatggaa    3960
cgcatccaac cagttcactg gatgggtcga cgtcaatctg accgaacagg gtgaggctga    4020
ggccaagcgc ggaggcgaac tcctcgtcga ggcaggcgtc ctcccaggcg ttgtatacac    4080
ctccttgctg cgtcgcgcga tc                                             4102
```

<210> SEQ ID NO 16
<211> LENGTH: 3181
<212> TYPE: DNA
<213> ORGANISM: Artificial Sequence
<220> FEATURE:
<223> OTHER INFORMATION: pEC-M24

<400> SEQUENCE: 16

```
gatcgccggg gcggacacct agtgcgcgca ggccagcggc agttttgcgg acttctttgt     60
ccagttcacc gtaggtttgt gaacgaccga aaaagtaggg ggctggcttg tctgcgttga    120
tggccaggtt gttgtcgtaa acgtccagca gggtggtgtc gccatattcc agcgagtgtg    180
gcgtccactc tgggtagtgc tggagccatt ctttggtttc gtatgctgac atggtgtccc    240
ttcaactgcg ttgctttagt gcccttttagt atatagagac gtcccgctgc tttcttcggc    300
gatctagaat gtgggcatgc gcgtagctat gatttccatg cacacctctc cattgcagca    360
gcccggaact ggtgattcag gcggcatgaa cgtctacatt ctttcgaccg cgactgagct    420
agcgaaacag gtatcgagg tcgatattta cactcgtgcc acgaggcctt ctcagggtga    480
gatcgtgaga gtagctgaga atttgcgggt cattaatatc gctgcggggc gtatgagggg    540
gctttccaaa gaggagcttc ctactcagtt ggcggcgttt accggcggaa tgttgtcgtt    600
tacgcgccgg gagaaggtta cttatgatct gatccattct cactattggc tgtctggtca    660
ggtggggtgg ttgctgcgcg atttgtggcg gattccccct attcatacgg cacacacttt    720
ggcggcggtg aagaattctt atcgggatga ttcggacact ccggagtcgg aggcgcgtcg    780
catttgtgag cagcagctgg tggataacgc tgacgtgttg gcggtgaaca ctcaggagga    840
gatgcaggat ttgatgcatc actacgatgc ggatccggat cggatttctg tggtgtcacc    900
gggtgcggac gtgaactttt atagccctgg aaatgatcgc gcgacggaac gttcccgtcg    960
tgagctgggc attccgctgc acacaaaggt agtggctttt gtgggtcggt tgcagccgtt   1020
taagggcccg caggtgctga tcaaggcggt tgcggcgttg tttgatcgcg atccggaccg   1080
aaatctgcgc gtcattattt gtggcggccc ttctggtccg aatgcgacac cggataccta   1140
taggcatatg gcagaggaac tgggcgtcga aaagcgaatt cgcttttttgg acccgcgccc   1200
gccgagcgag ctagtggccg tgtatcgggc ggcggacatc gtggccgtgc caagttttaa   1260
tgagtccttc ggactcgtcg ccatggaggc gcaagccagc ggcacaccgg tcattgcggc   1320
ccgggttggc ggcctgccca tcgcagtcgc ggaaggggag acgggattgc ttgtcgacgg   1380
ccactccccg catgcctggg ccgacgcctt agccacactc ttggacgatg acgaaacgcg   1440
catcagaatg ggtgaagacg ccgtcgaaca cgccagaaca ttctcctggg cggccaccgc   1500
cgcacagcta tcgtcgctgt acaacgcgcg tattgccaac gaaaatgtcg acggtgaaac   1560
gcatcacggc taagtaaacg cgcgtcgtgg aacataaagt ggcaaactag tacctatgac   1620
```

```
taacggaaaa ttgattcttc ttcgtcacgg tcagagcgaa tggaacgcat ccaaccagtt   1680
cactggatgg gtcgacgtca atctgaccga acagggtgag gctgaggcca agcgcggagg   1740
cgaactcctc gtcgaggcag gcgtcctccc aggcgttgta tacacctcct tgctgcgtcg   1800
cgcgatccgc actgcaaaca tcgcactgaa cgctgcagac cgccactgga tcccagtgat   1860
ccgcgactgg cgcctcaacg agcgtcacta cggcgcactg cagggccttg acaaggctgc   1920
aaccaaggaa aaatacggcg acgaccagtt catggaatgg cgccgctcct acgacacccc   1980
accaccagag ctcgcggatg acgcagagta ctcccaggca aatgaccctc gttacgcgga   2040
cctcgacgta gttccacgca ccgaatgcct caaggacgtt gtggttcgtt ttgttcctta   2100
cttcgaggaa gaaatcctgc cacgcgcaaa gaagggcgaa accgtcctca tcgcagcaca   2160
cggcaactcc ctgcgtgcgc tggttaagca ccttgacggc atctccgatg ctgatatcgc   2220
agagctcaac atcccaaccg gcatcccact ggtctacgaa atcgccgaag acggttccgt   2280
agtaaaccca ggcggcacct acctcgatcc tgaggcagca gcagccggcg cagcagcagt   2340
agcaaaccag ggtaataagt agctatttgt aggtgagcac tcttcttgct ttcgtattgg   2400
gcgtggtcct catgggcctc gccctacctg cgtatacgaa aattaaagat cggatgcgtc   2460
gccacaagtc cgcggtcacc ctgtccgaaa accaggtcac cacggtgggg caggtcctcc   2520
acctggcgat tcaaggctcc ccaacgggaa tcacggttgt cgatcgcacc ggcgacgtca   2580
tcttatccaa cggccgcgcc cacgaattgg gcatcgtcca cgaaagatcc gtcgacggca   2640
acgtttggcg cgtcgcccag gaagccttcc aagaccaaga aacccactca ctcgacgtcc   2700
acccagaccg caatccgcgg cgcccgggta gtcgcatcac cgcagtgcag gcagtggtca   2760
agcctttaac gcttatcgac gatcgtttcg tgatcatcta tgcctccgac gaatccgaaa   2820
acgtgcgcat ggaatcggca cgccgagact tcgtcgcaaa cgtctcccac gaactgaaaa   2880
cccccgtcgg cggcatggca ctcctcgcgg aagccctcat ggaatcctcc gacgacccag   2940
aacaagtcga atacttcgga tccaggctcc accgcgaagc ccaccgcatg gccgacatga   3000
tcaacgaact gatctccctt tccaaacttc agggcgccga acgactccct gatatggaac   3060
ccgtccaggc tgacgacatc atcagcgaag ccatcgaacg cacccaactc gccgccgaca   3120
acgccaacat cgaaatcatt cgcggcgacc gcaccggcgt ttgggtagaa gccgatcgat   3180
c                                                                   3181
```

MICROORGANISM OF THE GENUS *CORYNEBACTERIUM* PRODUCING L-LYSINE AND A METHOD FOR PRODUCING L-LYSINE USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_443USPC_SEQUENCE_LISTING.txt. The text file is 16 KB, was created on May 14, 2019, and is being submitted electronically via EFS-Web.

TECHNICAL FIELD

The present disclosure relates to a microorganism of the genus *Corynebacterium* producing L-lysine, and a method for producing L-lysine using the same.

BACKGROUND ART

L-Lysine is used in animal feed, and in the industries of pharmaceuticals and cosmetics for people, and it is commonly produced via fermentation using strains of the genus *Corynebacterium* or strains of the genus *Escherichia*. For the production of L-lysine, various studies for developing highly efficient production strains and fermentation process technology are underway. Specifically, methods directed to specific approaches to target materials, such as increasing the expression of genes encoding enzymes related to L-lysine biosynthesis, or deleting genes not necessary for its biosynthesis, are mainly used (Korean Patent No. 10-0838038).

In order to explore effective characteristics that can increase lysine productivity, the present inventors have discovered a gene associated with the high-concentration production of lysine by randomly introducing an endogenous gene of a microorganism of the genus *Corynebacterium*, and with this discovery, and confirmed that when the expression of this gene is increased in a microorganism of the genus *Corynebacterium*, the productivity of L-lysine can be increased, thereby completing the present disclosure.

DISCLOSURE

Technical Problem

An object of the present disclosure is to provide a microorganism of the genus *Corynebacterium* producing L-lysine, having an improved activity of a protein consisting of the amino acid sequence of SEQ ID NO: 1 compared to an endogenous activity.

Another object of the present disclosure is to provide a method for producing L-lysine using the microorganism.

Technical Solution

In order to achieve the above objects, an aspect of the present disclosure is a microorganism of the genus *Corynebacterium* producing L-lysine, having an improved activity of a protein consisting of the amino acid sequence of SEQ ID NO: 1 compared to an endogenous activity.

Hereinbelow, the present disclosure will be described in detail. Meanwhile, each of the explanations and exemplary embodiments disclosed herein can be applied to other explanations and exemplary embodiments. That is, all combinations of various factors disclosed herein belong to the scope of the present disclosure. Furthermore, the scope of the present disclosure should not be limited by the specific disclosure provided hereinbelow.

In the present disclosure, the term "protein consisting of the amino acid sequence of SEQ ID NO: 1" may be interchangeably used with the term "HM1524 protein". Additionally, it may be interchangeably used with the term "protein encoded by the HM1524 gene". In addition, the expression "protein essentially consisting of the amino acid sequence of SEQ ID NO: 1" or "protein composed of the amino acid sequence of SEQ ID NO: 1" may be interchangeably used.

Additionally, the protein may include a polypeptide having a homology to the amino acid sequence of SEQ ID NO: 1 of at least 80%, 90%, 95%, 97%, or 99%. For example, it is apparent that a protein having an amino acid sequence in which the sequence is partially deleted, modified, substituted, or inserted is included in the scope of the present disclosure, as long as it has an amino acid sequence having the above homology and exhibiting an effect corresponding to the protein consisting of the amino acid sequence of SEQ ID NO: 1.

In addition, as long as it has an activity corresponding to that of the protein consisting of the amino acid sequence of SEQ ID NO: 1, a mutation that can occur by a meaningless sequence addition upstream or downstream of the amino acid sequence of the amino acid sequence of SEQ ID NO: 1 or a naturally occurring mutation therein, or a silent mutation therein, is not excluded, and a protein having the amino acid sequence of SEQ ID NO: 1 is also included in the scope of the present disclosure.

As used in the present disclosure, the term "homology" refers to the percentage of identity between two polynucleotide or polypeptide moieties, indicating the degree of correspondence to a given amino acid sequence or nucleotide sequence, and may be expressed as a percentage. In the present specification, a homologous sequence of the given amino acid sequence or nucleotide sequence having an activity the same as or similar to that of the given amino acid sequence or nucleotide sequence may be indicated in terms of "% homology". For example, the homology may be confirmed using standard software for calculating parameters such as score, identity, and similarity, specifically, BLAST 2.0, or by comparing sequences by southern hybridization experiments under defined stringent conditions, and the defined appropriate hybridization conditions are within the relevant technical scope and may be determined by a method known to those skilled in the art (e.g., J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York).

A gene encoding the protein consisting of the amino acid sequence of SEQ ID NO: 1, although not limited thereto, may be a polynucleotide including the nucleotide sequence of SEQ ID NO: 2, and may be a polynucleotide having a homology to the nucleotide sequence of SEQ ID NO: 2 of at least 80%, 90%, 95%, 97%, or 99%. It is apparent that polynucleotides which, due to codon degeneracy, can be translated into the protein consisting of the amino acid sequence of SEQ ID NO: 1 or proteins having a homology thereto can also be included. Alternatively, a probe which can be prepared from a known gene sequence, for example, any sequence which hybridizes with a sequence complementary to all or part of the nucleotide sequence under stringent conditions to encode a protein having the activity of the protein consisting of the amino acid sequence of SEQ ID NO: 1, may be included without limitation. The term "stringent conditions" refers to conditions which allow specific hybridization between polynucleotides. Such conditions are specifically described in the literature (e.g., J. Sambrook et al., infra). For example, the stringent conditions may include conditions under which genes having a high homology, a homology of 80% or higher, specifically 90% or higher, more specifically 95% or higher, much more specifically 97% or higher, and particularly specifically 99% or higher hybridize with each other, while genes having a homology lower than the above homology do not hybridize with each other; or may include ordinary washing conditions of Southern hybridization, i.e., washing once, specifically two or three times, at a salt concentration and a temperature corresponding to 60° C., 1×SSC, and 0.1% SDS; specifically 60° C., 0.1×SSC, and 0.1% SDS; and more specifically 68° C., 0.1×SSC, and 0.1% SDS.

Hybridization requires that two nucleic acids contain complementary sequences, although mismatches between nucleotides may be possible depending on the stringency of the hybridization. The term "complementary" is used to describe the relationship between nucleotides that can hybridize with each other. For example, with respect to DNA, adenosine is complementary to thymine, and cytosine is complementary to guanine. Therefore, the present disclosure may also include an isolated nucleic acid fragment complementary to the entire sequence as well as a nucleic acid sequence substantially similar thereto.

Specifically, the polynucleotide having homology may be detected using hybridization conditions including a hybridization step at a $T_m$ value of 55° C. under the above-described conditions. Further, the $T_m$ value may be 60° C., 63° C., or 65° C., but is not limited thereto, and may be appropriately controlled by those skilled in the art depending on the purpose thereof.

The appropriate stringency for hybridizing polynucleotides depends on the length and degree of complementarity of the polynucleotides, and these variables are well known in the art. The probe used in the hybridization may be part of a sequence complementary to the nucleotide sequence. Such probe may be manufactured via PCR using an oligonucleotide prepared based on a known sequence as a primer and a gene fragment containing the nucleotide sequence as a template. The gene fragment may be, for example, at least about 50 nucleotides, 60 nucleotides, 70 nucleotides, 80 nucleotides, 90 nucleotides, or at least 100 nucleotides. Additionally, those skilled in the art may adjust the temperature and salt concentration of washing solutions as needed depending on factors such as the length of the probe.

As used in the present disclosure, the term "endogenous activity" refers to the particular activity of a protein originally possessed by the parental strain of a microorganism prior to transformation thereof, in the case that the property of the microorganism changes through genetic modification due to natural or artificial factors.

As used in the present disclosure, the term "activity which is improved compared to an endogenous activity" refers to the enhancement of the activity of a protein of a microorganism compared to its endogenous activity or its activity prior to modification. The improvement of activity may include both introduction of foreign HM1524 and endogenous enhancement of the activity of HM1524.

Specifically, the improvement of activity in the present disclosure may be performed by the following methods:

1) a method for increasing the copy number of the polynucleotide encoding the protein,
2) a method for modifying an expression regulatory sequence such that the expression of the polynucleotide is increased,
3) a method for modifying the polynucleotide sequence on a chromosome such that the activity of the protein is enhanced,
4) a method for introducing a modified polynucleotide in which the codons of a foreign polynucleotide or the above polynucleotide exhibiting the activity of the protein have been optimized, or
5) a method for modification to effect enhancement by a combination of the above methods, etc.; however, the improvement of activity is not limited thereto.

The increasing of the copy number of the polynucleotide in method 1) above may be performed by operable linkage to a vector, or may be performed by insertion into a chromosome in a host cell, but is not particularly limited thereto. Specifically, it may be performed by operably linking the polynucleotide encoding the protein of the present disclosure to a vector which can replicate and function regardless of the host cell, and introduction thereof into the host cell. Alternatively, it may be performed by a method for increasing the copy number of the polynucleotide in the chromosome in the host cell by operably linking the polynucleotide to a vector which can insert the polynucleotide into the chromosome in the host cell, and introduction thereof into the host cell.

In addition, in method 2) above, the modification of an expression regulatory sequence such that expression of the polynucleotide increases may be performed by inducing a modification in the sequence through deletion, insertion, or non-conservative or conservative substitution of a nucleic acid sequence, or through a combination thereof in order to further enhance the activity of the expression regulatory sequence, or by replacement with a nucleic acid sequence having a stronger activity, but is not particularly limited thereto. The expression regulatory sequence may include a promoter, an operator sequence, a sequence coding for a ribosome-binding site, a sequence regulating the termination of transcription and translation, etc., but is not particularly limited thereto.

A strong heterologous promoter may be linked to the upstream region of the expression unit of the polynucleotide instead of the original promoter; examples of the strong promoters are CJ7 promoter (Korean Patent No. 0620092 and International Publication No. WO2006/065095), lysCP1 promoter (International Publication No. WO2009/096689), EF-Tu promoter, groEL promoter, aceA or aceB promoter, etc., but the strong promoter is not limited thereto. Further, in method 3) above, the modification of the polynucleotide sequence on a chromosome may be performed by inducing modification on the expression regulatory sequence by deletion, insertion, or non-conservative or conservative substitution of a nucleic acid sequence, or through a combination thereof, so as to further enhance the activity of the polynucleotide sequence, or it may be performed by replacement of the polynucleotide sequence with a polynucleotide sequence modified to have further stronger activity; however, the modification is not particularly limited thereto.

Additionally, in method 4) above, the introduction of a foreign polynucleotide sequence may be performed by introducing into a host cell a foreign polynucleotide encoding a protein that exhibits activity the same as or similar to that of the protein above, or a modified polynucleotide in which the codons of the foreign polynucleotide have been optimized.

The foreign polynucleotide may be used without limitation to its origin or sequence as long as it exhibits activity the same as or similar to that of the protein. Additionally, for the optimized transcription and translation of the foreign polynucleotide in a host cell, it may be introduced into a host cell after optimization of its codons. The introduction may be performed by those skilled in the art by selecting a suitable transformation method known in the art, and through expression of the introduced polynucleotide in the host cell, the protein can be produced, thereby improving its activity.

Finally, method 5), which relates to modification to effect enhancement by a combination of methods 1) to 4), may be performed by combined application of at least one among the following: increasing the copy number of the polynucleotide encoding the protein, modifying an expression regulatory sequence such that expression of the polynucleotide increases, modifying the polynucleotide sequence on a chromosome, and modifying a foreign polynucleotide exhibiting the activity of the protein or a codon-optimized modified polynucleotide thereof.

As used herein, the term "vector" refers to a DNA construct including a polynucleotide sequence encoding the target protein, which is operably linked to a suitable regulatory sequence such that the target protein can be expressed in an appropriate host. The regulatory sequence includes a promoter capable of initiating transcription, any operator sequence for the control of the transcription, a sequence encoding an appropriate mRNA ribosome-binding domain, and a sequence controlling the termination of transcription and translation. After being transformed into a suitable host cell, the vector may be replicated or function irrespective of the host genome, and it may be integrated into the host genome itself. In an embodiment, a polynucleotide encoding a target protein in the chromosome may be replaced with a modified polynucleotide through a vector for chromosomal insertion. The insertion of the polynucleotide into the chromosome may be performed by any method known in the art, e.g., homologous recombination, but is not limited thereto.

The vector used in the present disclosure is not particularly limited, and any vector known in the art may be used. Examples of conventionally used vectors may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc., may be used, and as a plasmid vector, those based on pBR, pUC, pBluescriptII, pGEM, pTZ, pCL, pET, etc. may be used. Specifically, the vectors pDZ, pACYC177, pACYC184, pCL, pECCG117, pUC19, pBR322, pMW118, pCC1BAC, etc. may be used.

As used herein, the term "transformation" refers to a process of introducing a vector including a polynucleotide encoding a target protein into a host cell, thereby enabling expression of the protein encoded by the polynucleotide in the host cell. As long as the transformed polynucleotide can be expressed in the host cell, it does not matter whether it is inserted into the chromosome of a host cell and located therein or located outside the chromosome, and both cases may be included. Additionally, the polynucleotide includes DNA and RNA which encode the target protein. The polynucleotide may be introduced in any form as long as it can be introduced into a host cell and expressed therein. For example, the polynucleotide may be introduced into a host cell in the form of an expression cassette, which is a gene construction including all elements necessary for self-expression. The expression cassette may conventionally include a promoter operably linked to the polynucleotide, a terminator, a ribosome-binding site, and a stop codon. The expression cassette may be in the form of an expression vector capable of self-replication. Additionally, the polynucleotide may be introduced into a host cell as is and operably linked to a sequence necessary for its expression in the host cell, but is not limited thereto.

Additionally, as used above, the term "operably linked" refers to a functional linkage between the above gene sequence and a promoter sequence which initiates and mediates the transcription of the polynucleotide encoding the target protein of the present disclosure.

The method for transforming the vector of the present disclosure includes any method of introducing a nucleic acid into a cell, and may be performed by selecting a suitable standard technique known in the art according to the host cell. Examples of the method include electroporation, calcium phosphate ($CaHPO_4$) precipitation, calcium chloride ($CaCl_2$) precipitation, microinjection, a polyethylene glycol (PEG) technique, a DEAE-dextran technique, a cationic liposome technique, a lithium acetate-DMSO technique, etc., but the method is not limited thereto.

As the host cell, it is preferable to use a host having high DNA introduction efficiency and high expression efficiency for the introduced DNA; for example, the host cell may be a microorganism of the genus *Corynebacterium*.

As used herein, the term "L-lysine" refers to a basic α-amino acid which, as an essential amino acid, cannot be synthesized in vivo, and which is an L-amino acid with the chemical formula $NH_2(CH_2)_4CH(NH_2)COOH$. Additionally, the L-lysine may be included in the scope of the present disclosure even when in the form of a salt.

As used herein, the term "L-lysine-producing microorganism" refers to a microorganism strain which can produce L-lysine in view of the objects of the present disclosure, specifically refers to a strain which can produce L-lysine in a high concentration via the manipulation according to the present disclosure. Accordingly, so long as the microorganism is capable of producing L-lysine, the type of its parental strain is not particularly limited. That is, in the present disclosure, the parental strain may include both strains with L-lysine productivity and those without L-lysine productivity. The L-lysine productivity may include both that which occurs naturally or that which has been artificially engineered. The microorganism having artificially engineered L-lysine productivity may be modified to have L-lysine productivity by way of a mutation-inducing substance such as nitrosoguanidine (NTG), etc., or the expression level or activity of a special-purpose protein may be controlled to obtain L-lysine productivity, but the microorganism is not limited thereto. Specifically, the special-purpose protein may include all proteins that directly/indirectly act along the L-lysine biosynthetic pathway, and by increasing or decreasing the expression level or activity thereof, the microorganism may be modified to have L-lysine productivity; additionally, modification may also be induced in the amino acid sequence or nucleotide sequence of such protein to obtain L-lysine productivity. The artificial engineering of the microorganism, including the control of expression of a special-purpose protein and induction of random mutation using NTG, etc. described above, may be appropriately performed via a known technique by those skilled in the art.

The microorganism may specifically be a microorganism of the genus *Corynebacterium*. For example, *Corynebacterium glutamicum*, *Corynebacterium ammoniagenes*, *Corynebacterium thermoaminogenes*, *Brevibacterium flavum*, or *Brevibacterium fermentum*, etc. may be used, but the microorganism is not limited thereto. For example, *Corynebacterium glutamicum* may be used as the microorganism of the genus *Corynebacterium*. However, the microorganism is not limited to these examples, and other known microorganisms of the genus *Corynebacterium* having L-lysine productivity may be used.

Examples of the known microorganisms of the genus *Corynebacterium* having L-lysine productivity are the microorganisms described in Korean Patent No. 10-0397322 (or U.S. Patent Publication No. 2003-0124688), Korean Patent No. 10-0924065 (or U.S. Patent Publication No. 2010-0143984), Korean Patent No. 10-0073610, and/or Binder et al., Genome Biology 2012, 13:R40, and the contents of these are incorporated by reference herein in their entirety.

As another aspect, the present disclosure provides a method for producing L-lysine, comprising: culturing a microorganism of the genus *Corynebacterium* producing L-lysine, having an improved activity of a protein consisting of the amino acid sequence of SEQ ID NO: 1 compared to an endogenous activity, in a medium; and recovering L-lysine from the cultured microorganism or medium thereof.

The microorganism of the genus *Corynebacterium* producing L-lysine is as described above.

As used herein, the term "culturing" means growing the microorganism under appropriately controlled environmental conditions. The culture process of the present disclosure can be performed according to suitable culture media and culture conditions known in the art. Such culture process can be easily adjusted for use by those skilled in the art according to the strain to be selected. In the method above, the culturing of the microorganism may be performed by a known batch culture method, continuous culture method, fed-batch culture method, etc., but is not limited thereto. In particular, with respect to the culture conditions, the pH of the culture may be adjusted to a suitable pH (e.g., pH 5 to pH 9, specifically pH 6 to pH 8, and most specifically pH 6.8) using a basic compound (e.g., sodium hydroxide, potassium hydroxide, or ammonia) or acidic compound (e.g., phosphoric acid or sulfuric acid). Additionally, during the culturing, an antifoaming agent such as a fatty acid polyglycol ester may be added to prevent foam generation; further, oxygen or oxygen-containing gas may be injected into the culture in order to maintain an aerobic state thereof, or, in order to maintain an anaerobic or microaerobic state of the culture, nitrogen, hydrogen, or carbon dioxide gas may be injected, or the culturing may be performed without the injection of gas. The culture temperature may be maintained at 20° C. to 45° C., specifically at 25° C. to 40° C., and the culturing may be continued until a desired amount of useful material produced is obtained, specifically for approximately 10 to 160 hours. However, the culture is not limited to the above. The L-lysine produced by way of the culturing may be secreted in the medium or may remain in the cells.

Additionally, as a carbon source for the culture medium to be used, sugars and carbohydrates (e.g., glucose, sucrose, lactose, fructose, maltose, molasses, starch, and cellulose), oils and fats (e.g., soybean oil, sunflower oil, peanut oil, and coconut oil), fatty acids (e.g., palmitic acid, stearic acid, and linoleic acid), alcohols (e.g., glycerol and ethanol), organic acids (e.g., acetic acid), etc. may be used alone or in combination, but the carbon source is not limited thereto. As a nitrogen source, nitrogen-containing organic compounds (e.g., peptone, yeast extract, meat gravy, malt extract, corn steep liquor, soybean flour, and urea) or inorganic compounds (e.g., ammonium sulfate, ammonium chloride, ammonium phosphate, ammonium carbonate, and ammonium nitrate), etc. may be used alone or in combination, but the nitrogen source is not limited thereto. As a phosphorus source, potassium dihydrogen phosphate, dipotassium hydrogen phosphate, corresponding sodium-containing salts, etc. may be used alone or in combination, but the phosphorus source is not limited thereto. In addition, essential growth-promoting materials such as other metal salts (e.g., magnesium sulfate or iron sulfate), amino acids, vitamins, etc. may be contained in the medium.

In the method of the present disclosure for recovering the L-lysine produced in the culturing, the target amino acid may be collected from the culture broth using an appropriate method known in the art according to the culture method. For example, centrifugation, filtration, anion-exchange chromatography, crystallization, HPLC, etc. may be used, and the target L-lysine may be recovered from the medium or microorganism using an appropriate method known in the art. Additionally, the recovering step may be included a purification process.

Advantageous Effects of the Invention

L-Lysine can be produced with high efficiency using the microorganism of the present disclosure, which has L-lysine productivity.

DETAILED DESCRIPTION OF THE INVENTION

Hereinafter, the present disclosure will be described in detail through exemplary embodiments. However, these exemplary embodiments are provided for the purpose of illustration only, and the scope of the present disclosure is not limited to these exemplary embodiments.

Example 1: Preparation of Wild-Type Library of Microorganism of Genus *Corynebacterium*

Upon extracting genomic DNA from *Corynebacterium glutamicum* ATCC13032, the genomic DNA was treated with Sau3AI restriction enzyme and the DNA fragments were separated by size through electrophoresis on agarose gel, and thereby DNA fragments of 3 kb to 4 kb were selectively obtained. After ligation of the fragments with pECCG117 vector (Korean Patent No. 10-0057684), which has a BamHI restriction site, and introduction into *E. coli* DH5α, the resultants were then plated on solid LB medium containing kanamycin (25 mg/L), and thus transformed colonies were obtained. PCR was performed on 100 random colonies using primers of SEQ ID NOs: 3 and 4, and thereby it was found that the ratio of the colonies containing the vector in which the target DNA fragments of approximately 3 kb to 4 kb were inserted was 90% or higher. All of the obtained colonies were co-cultured after inoculation in kanamycin (25 mg/L)-containing liquid LB medium; plasmids were then extracted using a commonly known plasmid extraction method, thereby completing the *Corynebacterium glutamicum* ATCC13032 genomic DNA library.

```
SEQ ID NO: 3:
5'-ACGACGGGATCAGTACCGA-3'

SEQ ID NO: 4:
5'-AGCTATCTGTCGCAGCGCC-3'
```

Example 2: Preparation and Evaluation of Lysine-Producing Microorganism Introduced with Wild-Type Library Using an electric pulse method, the genomic DNA library prepared in Example 1 was introduced into the lysine-producing strain *Corynebacterium glutamicum* KCCM11016P (originally designated as KFCC10881, the microorganism was re-deposited at an international depositary institution under the Budapest Treaty and designated as Accession No. KCCM11016P; Korean Patent No. 10-0159812), and after plating on a complex plate medium containing kanamycin (25 mg/L) and culturing at 30° C. for 24 hours, approximately 2,000 colonies were obtained.

<Complex Plate Medium>

20 g glucose, 50 g $(NH_4)_2SO_4$, 10 g peptone, 5 g yeast extract, 1.5 g urea, 5 g $KH_2PO_4$, 10 g $K_2HPO_4$, 0.5 g $MgSO_4.7H_2O$, 100 μg biotin, 1000 μg thiamine HCl, 2000 μg calcium pantothenate, 2000 μg nicotinamide, 20 g agar, 25 mg kanamycin (per 1 L distilled water)

200 μL of a complex liquid medium was dispensed into each well of a 96-well cell culture plate, and after inoculation of each of the obtained colonies, shake-culturing was performed for 24 hours under conditions of 30° C. and 1200 rpm. The cell bodies and supernatant were separated by centrifugation of the culture broth, and 50 μL of the supernatant was mixed with a reaction solution containing lysine oxidase.

<Complex Liquid Medium>

20 g glucose, 10 g peptone, 5 g yeast extract, 1.5 g urea, 4 g $KH_2PO_4$, 8 g $K_2HPO_4$, 0.5 g $MgSO_4.7H_2O$, 100 μg biotin, 1000 μg thiamine HCl, 2000 μg calcium pantothenate, 2000 μg nicotinamide, 25 mg kanamycin (per 1 L distilled water)

<Reaction Solution>

0.02 units lysine oxidase (Sigma-Aldrich), 0.2 units peroxidase (Sigma-Aldrich), 2 mg ABTS (per 1 mL potassium phosphate buffer solution)

Thereafter, absorbance at $OD_{405}$ was analyzed for 30 minutes, and 15 experimental groups exhibiting higher absorbance than the control group (KCCM11016P/pECCG117) were selected. In order to confirm the lysine productivity of each transformant, each strain was inoculated in a 250 mL corner-baffle flask containing 25 mL of a kanamycin (25 mg/L)-containing seed medium and shake-cultured for 20 hours under conditions of 30° C. and 200 rpm. 1 mL of the seed culture broth was inoculated in a 250 mL corner-baffle flask containing 24 mL of a kanamycin (25 mg/L)-containing production medium and shake-cultured for 96 hours at 37° C. and 200 rpm. After termination of the culturing, L-lysine concentration was analyzed using HPLC (Table 1).

<Seed Medium>

20 g glucose, 5 g $(NH_4)_2SO_4$, 10 g peptone, 5 g yeast extract, 1.5 g urea, 4 g $KH_2PO_4$, 8 g $K_2HPO_4$, 0.5 g $MgSO_4.7H_2O$, 100 μg biotin, 1000 μg thiamine HCl, 2000 μg calcium pantothenate, 2000 μg nicotinamide (per 1 L distilled water)

<Production Medium (pH 7.0)>

100 g glucose, 40 g $(NH_4)_2SO_4$, 2.5 g soybean protein, 5 g corn steep solids, 3 g urea, 1 g $KH_2PO_4$, 0.5 g $MgSO_4.7H_2O$, 100 μg biotin, 1000 μg thiamine HCl, 2000 μg calcium pantothenate, 3000 μg nicotinamide, 30 g $CaCO_3$ (per 1 L distilled water)

TABLE 1

| Strain | No. | Lysine concentration (g/L) | Average lysine concentration (g/L) | Strain | No. | Lysine concentration (g/L) | Average lysine concentration (g/L) |
|---|---|---|---|---|---|---|---|
| KCCM11Q16P/pECCG117 | 1 | 43.2 | 43.8 | KCCM11016P/M24 | 1 | 46.8 | 46.5 |
|  | 2 | 44.3 |  |  | 2 | 46.0 |  |
|  | 3 | 43.9 |  |  | 3 | 46.7 |  |
| KCCM11016P/A56 | 1 | 43.5 | 43.4 | KCCM11016P/O9 | 1 | 44.0 | 43.8 |
|  | 2 | 44.3 |  |  | 2 | 43.8 |  |
|  | 3 | 42.5 |  |  | 3 | 43.6 |  |
| KCCM11016P/C2 | 1 | 41.8 | 42.2 | KCCM11016P/O21 | 1 | 43.1 | 42.8 |
|  | 2 | 42.6 |  |  | 2 | 42.5 |  |
|  | 3 | 42.3 |  |  | 3 | 42.9 |  |
| KCCM11016P/D34 | 1 | 45.2 | 44.6 | KCCM11016P/P85 | 1 | 43.1 | 43.4 |
|  | 2 | 44.5 |  |  | 2 | 43.5 |  |
|  | 3 | 44.0 |  |  | 3 | 43.6 |  |
| KCCM11016P/F90 | 1 | 43.9 | 44.6 | KCCM11016P/P95 | 1 | 44.6 | 44.4 |
|  | 2 | 45.5 |  |  | 2 | 44.3 |  |
|  | 3 | 44.4 |  |  | 3 | 44.4 |  |
| KCCM11016P/H15 | 1 | 47.6 | 46.8 | KCCM11016P/R48 | 1 | 42.6 | 42.9 |
|  | 2 | 46.2 |  |  | 2 | 42.4 |  |
|  | 3 | 46.7 |  |  | 3 | 43.6 |  |
| KCCM11016P/J66 | 1 | 44.3 | 43.8 | KCCM11016P/S47 | 1 | 42.5 | 41.7 |
|  | 2 | 43.5 |  |  | 2 | 41.0 |  |
|  | 3 | 43.6 |  |  | 3 | 41.6 |  |
| KCCM11016P/K14 | 1 | 42.9 | 43.4 | KCCM11016P/U77 | 1 | 43.7 | 43.9 |
|  | 2 | 43.5 |  |  | 2 | 44.5 |  |
|  | 3 | 43.9 |  |  | 3 | 43.6 |  |

From the above results, KCCM11016P/H15 and KCCM11016P/M24 were selected, which showed an effect of increased lysine productivity compared to the control group, and plasmids were extracted using a commonly known plasmid extraction method. The plasmid derived from KCCM11016P/H15 was named pEC-H15, and that derived from KCCM11016P/M24 was named pEC-M24. Thereafter, nucleotide sequence analysis was carried out using the primers of SEQ ID NOs: 3 and 4. As a result, the pEC-H15 and pEC-M24 plasmids were found to contain the nucleotide sequences of SEQ ID NOs: 15 and 16, respectively. Thus, it was found that both of the above plasmids contain the nucleotide sequence of SEQ ID NO: 2, which encodes the amino acid sequence of SEQ ID NO: 1. Accordingly, the gene encoding the amino acid sequence of SEQ ID NO: 1 was named HM1524, and is hereinafter referred to as such.

Example 3: Preparation of HM1524 Gene Overexpression Vector

In order to confirm the effect of HM1524 found in Example 2, a vector for overexpressing the corresponding gene was prepared.

Based on the reported nucleotide sequences, primers designed to allow insertion of XhoI restriction sites at the 5' and 3' ends (SEQ ID NOs: 5 and 6, respectively) were synthesized in order to obtain the DNA fragment containing the region from about 200 bp upstream of the HM1524 start codon to about 50 bp downstream of the stop codon thereof, and PCR was performed using the genomic DNA of *Corynebacterium glutamicum* as a template. PCR was performed by initial denaturation at 94° C. for 5 minutes; 30 cycles consisting of denaturation at 94° C. for 30 seconds, annealing at 56° C. for 30 seconds, and polymerization at 72° C. for 90 seconds; and final polymerization at 72° C. for 7 minutes.

```
SEQ ID NO: 5:
5'-TCACTCGAGTGATGGCCAGGTTGTTGTC-3'

SEQ ID NO: 6:
5'-TCACTCGAGTTAGTCATAGGTACTAGTTT-3'
```

After treatment of the above PCR amplification product with XhoI restriction enzyme, pECCG117 vector was treated with XhoI, ligated with the obtained DNA fragments, and transformed into *E. coli* DH5α, and the resultant was plated on solid LB medium containing kanamycin (25 mg/L). After PCR screening (using SEQ ID NOs: 3 and 4) of the colonies transformed with the vector in which the target gene was inserted, the plasmid was obtained using a commonly known plasmid extraction method, and this plasmid was named pECCG-HM1524.

Example 4: Analysis of Lysine Productivity of Strain Introduced with IIM1524 Gene Overexpression Vector Upon introduction of the pECCG-HM1524 vector prepared in Example 3 into *Corynebacterium glutamicum* KCCM11016P (i.e., lysine-producing strain) using an electric pulse method, the resultants were plated on the kanamycin (25 mg/L)-containing complex plate medium, and colonies were obtained after culturing for 24 hours at 30° C. The obtained strain was named KCCM11016P/pECCG-HM1524, and the L-lysine concentration of the culture broth was analyzed after culturing three batches according to the flask culture method of Example 2 (Table 2).

TABLE 2

| Strain | No. | Batch 1 Lysine concentration (g/L) | Batch 1 Average lysine concentration (g/L) | Batch 2 Lysine concentration (g/L) | Batch 2 Average lysine concentration (g/L) | Batch 3 Lysine concentration (g/L) | Batch 3 Average lysine concentration (g/L) |
|---|---|---|---|---|---|---|---|
| KCCM11016P | 1 | 43.9 | 44.0 | 43.5 | 43.9 | 43.1 | 43.6 |
|  | 2 | 44.2 |  | 43.7 |  | 43.9 |  |
|  | 3 | 43.8 |  | 44.5 |  | 43.8 |  |
| KCCM11016P/ pECCG-HM1524 | 1 | 46.8 | 46.9 | 45.6 | 46.2 | 46.5 | 46.3 |
|  | 2 | 46.5 |  | 46.8 |  | 45.1 |  |
|  | 3 | 47.5 |  | 46.1 |  | 47.2 |  |

As a result, it was found that the lysine productivity of KCCM11016P/pECCG-HM1524, the strain in which the HM1524 gene was overexpressed, was increased by 6% compared to that of the parental strain, KCCM11016P.

Example 5: Preparation of Vector for Further Chromosomal Insertion of HM1524 Gene In order to confirm the effect of the HM1524 gene found in Example 4, a vector was prepared for further insertion of the gene on the chromosome of *Corynebacterium*. In order to amplify Pcj7 promoter, derived from *Corynebacterium ammoniagenes* (Korean Patent No. 10-0620092), primers were synthesized which were designed to allow insertion of an EcoRI restriction site at the 5' end and an NdeI restriction site at the 3' end of the Pcj7 promoter (SEQ ID NOs: 7 and 8, respectively), and to allow insertion of a SpeI restriction site at the 5' end and a SalI restriction site at the 3' end of the Pcj7 promoter (SEQ ID NOs: 9 and 10, respectively). As a result of performing PCR using the synthesized primers (SEQ ID NOs: 7 and 8, and SEQ ID NOs: 9 and 10) with the genomic DNA of *Corynebacterium ammoniagenes* as a template, Pcj7 promoter DNA fragments were obtained containing EcoRI and NdeI restriction sites at the 5' and 3' ends, respectively, as well as SpeI and SalI restriction sites at the 5' and 3' ends, respectively. PCR was performed by initial denaturation at 94° C. for 5 minutes; 30 cycles consisting of denaturation at 94° C. for 30 seconds, annealing at 56° C. for 30 seconds, and polymerization at 72° C. for 30 seconds; and final polymerization at 72° C. for 7 minutes.

Based on the reported nucleotide sequences, primers designed to allow insertion of an NdeI restriction site at the start codon position and a SpeI restriction site downstream of the stop codon (SEQ ID NOs: 11 and 12, respectively) were synthesized in order to amplify the ORF of the HM1524 gene. As a result of performing PCR using the primers of SEQ ID NOs: 11 and 12 with the genomic DNA of *Corynebacterium glutamicum* ATCC13032 as a template, HM1524 gene DNA fragments were obtained containing NdeI and SpeI restriction sites at the start codon position and downstream of the stop codon, respectively. PCR was performed by initial denaturation at 94° C. for 5 minutes; 30 cycles consisting of denaturation at 94° C. for 30 seconds, annealing at 56° C. for 30 seconds, and polymerization at 72° C. for 90 seconds; and final polymerization at 72° C. for 7 minutes.

SEQ ID NO: 7:
5'-TCAGAATTCTTCCTTCAGGCTAATCTTTT-3'

SEQ ID NO: 8:
5'-TCACATATGTGTTTCCTTTCGTTGGGTAC-3'

SEQ ID NO: 9:
5'-TCAACTAGTCTTCCTTCAGGCTAATCTTT-3'

SEQ ID NO: 10:
5'-TCAGTCGACTGTTTCCTTTCGTTGGGTAC-3'

SEQ ID NO: 11:
5'-TCACATATGCGCGTAGCTATGATTTC-3'

SEQ ID NO: 12:
5'-TCAACTAGTTTAGCCGTGATGCGTTTCAC-3'

Upon treatment of each of the above three PCR amplification products with the restriction enzymes corresponding to the restriction sites at each end, pDZ vector (Korean Patent No. 10-0924065) was ligated to the DNA fragments, which were obtained after treatment with EcoR and SalI restriction enzymes, and thereby pDZ-Pcj7-HM1524 vector was prepared.

Example 6: Analysis of Lysine Productivity of Strain with Further Chromosomal Insertion of HM1524 Gene The pDZ-Pcj7-HM1524 vector prepared in Example 5 was introduced into *Corynebacterium glutamicum* KCCM11016P using an electric pulse method, and among the colonies transformed by way of homologous recombination, those in which the HM1524 gene was inserted downstream of the HM1524 gene stop codon on the chromosome were selected. The primers of SEQ ID NOs: 13 and 14 were used for screening of the colonies by PCR. The selected strain was named KCCM11016P::Pcj7-HM1524, and the L-lysine concentration of the culture broth was analyzed after culturing according to the flask culture method of Example 2 (Table 3).

SEQ ID NO: 13:
5'-GTCGAACACGCCAGAACATT-3'

SEQ ID NO: 14:
5'-TACTCTCACGATCTCACCCT-3'

TABLE 3

| Strain | No. | Batch 1 Lysine concentration (g/L) | Batch 1 Average lysine concentration (g/L) | Batch 2 Lysine concentration (g/L) | Batch 2 Average lysine concentration (g/L) | Batch 3 Lysine concentration (g/L) | Batch 3 Average lysine concentration (g/L) |
|---|---|---|---|---|---|---|---|
| KCCM11016P | 1 | 45.4 | 44.9 | 44.5 | 44.6 | 44.3 | 44.5 |
|  | 2 | 44.8 |  | 44.3 |  | 45.1 |  |
|  | 3 | 44.5 |  | 44.9 |  | 44.1 |  |
| KCCM11016P:: pcj-HM1524 | 1 | 47.7 | 47.4 | 46.8 | 47.1 | 4.72 | 47.2 |
|  | 2 | 47.1 |  | 47.5 |  | 46.9 |  |
|  | 3 | 47.5 |  | 47.1 |  | 47.4 |  |

As a result, it was found that the lysine productivity of KCCM11016P::Pcj7-HM1524, the strain in which the HM1524 gene was further inserted, was increased by about 6% compared to that of the parental strain, KCCM11016P.

The KCCM11016P::Pcj7-HM1524 strain was named CA01-2297, and was deposited at the Korean Culture Center of Microorganisms (KCCM), an international depositary institution under the Budapest Treaty, on Aug. 2, 2016, being designated as Accession No. KCCM11876P.

Example 7: Production of Lysine Using KCCM10770P-Derived Microorganism in Which HM1524 Gene is Further Inserted The pDZ-Pcj7-HM1524 vector prepared in Example 5 was transformed into *Corynebacterium glutamicum* KCCM10770P, a lysine-producing strain (Korean Patent No. 10-0924065). The above *Corynebacterium glutamicum* KCCM10770P features in that 7 genes associated with the L-lysine biosynthetic pathway are inserted on its chromosome. Colonies were selectively isolated by PCR, and the strain introduced with the HM1524 gene was named *Corynebacterium glutamicum* KCCM10770P::Pcj7-HM1524. Thereafter, the L-lysine concentration of the culture broth was analyzed after culturing according to the flask culture method of Example 2 (Table 4).

TABLE 4

| Strain | No. | Batch 1 Lysine concentration (g/L) | Batch 1 Average lysine concentration (g/L) | Batch 2 Lysine concentration (g/L) | Batch 2 Average lysine concentration (g/L) | Batch 3 Lysine concentration (g/L) | Batch 3 Average lysine concentration (g/L) |
|---|---|---|---|---|---|---|---|
| KCCM10770P | 1 | 45.7 | 46.1 | 45.8 | 45.9 | 45.8 | 45.5 |
|  | 2 | 46.3 |  | 46.2 |  | 45.1 |  |
|  | 3 | 46.2 |  | 45.8 |  | 45.7 |  |
| KCCM10770P:: Pcj-HM1524 | 1 | 47.8 | 48.3 | 48.5 | 48.1 | 47.5 | 47.7 |
|  | 2 | 48.5 |  | 47.5 |  | 47.5 |  |
|  | 3 | 48.7 |  | 48.2 |  | 48.1 |  |

As a result, it was found that the lysine productivity of the strain *Corynebacterium glutamicum* KCCM10770P::Pcj7-HM1524 was increased by about 5% compared to that of the parental strain.

Example 8: Production of Lysine Using CJ3P-Derived Microorganism in which HM1524 Gene is Further Inserted The pDZ-Pcj7-HM1524 vector prepared in Example 5 was transformed into *Corynebacterium glutamicum* CJ3P, a lysine-producing strain (Binder et al. Genome Biology 2012, 13:R40). *Corynebacterium glutamicum* CJ3P features in that 3 genes associated with the enhancement of L-lysine productivity are inserted on its chromosome. Colonies were selectively isolated by PCR, and the strain introduced with the HM1524 gene was named *Corynebacterium glutamicum* CJ3P::Pcj7-HM1524. The L-lysine concentration of the culture broth was analyzed after culturing according to the flask culture method of Example 2 (Table 5).

TABLE 5

| Strain | No. | Batch 1 | | Batch 2 | | Batch 3 | |
|---|---|---|---|---|---|---|---|
| | | Lysine concentration (g/L) | Average lysine concentration (g/L) | Lysine concentration (g/L) | Average lysine concentration (g/L) | Lysine concentration (g/L) | Average lysine concentration (g/L) |
| CJ3P | 1 | 8.0 | 8.0 | 7.5 | 8.4 | 8.1 | 8.1 |
| | 2 | 7.5 | | 8.5 | | 7.9 | |
| | 3 | 8.6 | | 9.1 | | 8.2 | |
| CJ3P:: Pcj7-HM1524 | 1 | 11.5 | 11.2 | 10.5 | 11.4 | 11.5 | 11.2 |
| | 2 | 11.2 | | 11.5 | | 11.4 | |
| | 3 | 10.9 | | 12.1 | | 10.6 | |

As a result, it was found that the lysine productivity of the strain *Corynebacterium glutamicum* CJ3P::Pcj7-HM1524 was increased by about 38% compared to that of the parental strain.

Example 9: Production of Lysine Using KCCM11347P-Derived Microorganism in Which HM1524 Gene is Further Inserted The pDZ-Pcj7-HM1524 vector prepared in Example 5 was transformed into *Corynebacterium glutamicum* KCCM11347P, a lysine-producing strain (originally designated as KFCC10750, the microorganism was re-deposited at an international depositary institution under the Budapest Treaty and designated as Accession No. KCCM11347P; Korean Patent No. 10-0073610). *Corynebacterium glutamicum* KCCM11347P features in that 3 genes associated with the enhancement of L-lysine productivity are inserted on its chromosome. Colonies were selectively isolated by PCR, and the strain introduced with the HM1524 gene was named *Corynebacterium glutamicum* KCCM11347P::Pcj7-HM1524. The L-lysine concentration of the culture broth was analyzed after culturing according to the flask culture method of Example 2 (Table 6).

TABLE 6

| Strain | No. | Batch 1 | | Batch 2 | | Batch 3 | |
|---|---|---|---|---|---|---|---|
| | | Lysine concentration (g/L) | Average lysine concentration (g/L) | Lysine concentration (g/L) | Average lysine concentration (g/L) | Lysine concentration (g/L) | Average lysine concentration (g/L) |
| KCCM11347P | 1 | 38.6 | 38.3 | 37.5 | 37.9 | 37.5 | 38.0 |
| | 2 | 37.8 | | 38.2 | | 38.6 | |
| | 3 | 38.5 | | 38.0 | | 37.9 | |
| KCCM11347P:: Pcj7-HM1524 | 1 | 41.5 | 41.9 | 42.1 | 41.9 | 41.6 | 41.7 |
| | 2 | 42.0 | | 41.9 | | 41.8 | |
| | 3 | 42.3 | | 41.6 | | 41.7 | |

As a result, it was found that the lysine productivity of the strain *Corynebacterium glutamicum* KCCM11347P::Pcj7-HM1524 was increased by about 10% compared to that of the parental strain.

Taken together, the above results demonstrate that for strains having improved activity of the HM1524 gene compared to an endogenous activity thereof, lysine productivity is improved, and further suggest that lysine can be produced in a large quantity by improving the activity of the protein encoded by the above gene in a microorganism.

From the foregoing, those skilled in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

[Accession No.]
Name of Depositary Institution: Korean Culture Center of Microorganisms (KCCM)
Accession No.: KCCM11876P
Date of Accession: Aug. 2, 2016

---

The invention claimed is:

1. An L-lysine producing microorganism of the genus *Corynebacterium*, having an improved activity of a protein consisting of the amino acid sequence of SEQ ID NO: 1 compared to its endogenous activity, wherein the improved activity is selected from the group consisting of: (1) an increased copy number of a polynucleotide encoding SEQ ID NO: 1; (2) increased expression of SEQ ID NO: 1 by modification of an expression regulatory sequence, (3) on a chromosome, modification of the expression regulatory sequence or introduction of an alternative expression regulatory sequence so that protein activity of SEQ ID NO: 1 is enhanced compared to prior to the modification, (4) codon optimization of the polynucleotide encoding SEQ ID NO: 1, and (5) combinations thereof; and wherein the improved activity of said SEQ ID NO: 1 results in increased L-lysine production in said *Corynebacterium* compared to an L-lysine producing *Corynebacterium* that is not modified to have said improved activity.

2. The L-lysine producing microorganism of the genus *Corynebacterium* according to claim 1, wherein the microorganism is *Corynebacterium glutamicum*.

3. A method for producing L-lysine, comprising: culturing an L-lysine producing microorganism of the genus *Corynebacterium*, having an improved activity of a protein consisting of the amino acid sequence of SEQ ID NO: 1 compared to its endogenous activity, in a medium; and recovering L-lysine from the cultured microorganism or medium thereof, wherein the improved activity is selected from the group consisting of: (1) an increased copy number of a polynucleotide encoding SEQ ID NO: 1; (2) increased expression of SEQ ID NO: 1 by modification of an expression regulatory sequence, (3) on a chromosome, modification of the expression regulatory sequence or introduction of an alternative expression regulatory sequence so that protein activity of SEQ ID NO: 1 is enhanced compared to prior to the modification, (4) codon optimization of the polynucleotide encoding SEQ ID NO: 1, and (5) combinations thereof;

and wherein the improved activity of said SEQ ID NO: 1 results in increased L-lysine production in said *Corynebacterium* compared to an L-lysine producing *Corynebacterium* that is not modified to have said improved activity.

4. The method for producing L-lysine according to claim 3, wherein the microorganism is *Corynebacterium glutamicum*.

* * * * *